United States Patent [19]
Kablaoui et al.

[11] 4,069,226
[45] Jan. 17, 1978

[54] PREPARATION OF ACYLISOXAZOLINES

[75] Inventors: Mahmoud S. Kablaoui, Wappingers Falls, N.Y.; John M. Larkin, Austin; Robert E. Reid, Houston, both of Tex.

[73] Assignee: Texaco Inc., New York, N.Y.

[21] Appl. No.: 739,377

[22] Filed: Nov. 5, 1976

[51] Int. Cl.$^2$ .......................................... C07D 261/04
[52] U.S. Cl. ................................. 260/307 F; 252/392
[58] Field of Search ..................................... 260/307 F

[56] References Cited

U.S. PATENT DOCUMENTS 2,564,423   8/1951   Barnum .................................. 106/14

*Primary Examiner*—Raymond V. Rush
*Attorney, Agent, or Firm*—Thomas H. Whaley; Carl G. Ries; George J. Darsa

[57] ABSTRACT

A method of preparing acylisoxazolines by contacting an alkene with dinitrogen tetroxide and oxygen in the presence of a denitrating agent and calcium oxide.

8 Claims, No Drawings

PREPARATION OF ACYLISOXAZOLINES

BACKGROUND OF THE INVENTION

This invention relates to a method of preparing acylisoxazolines. In particular, this invention relates to a novel method of preparing acylisoxazolines from 1-alkenes by means of a one-step procedure.

Acylisoxazolines may be prepared by the action of such acid, such as hydrochloric acid, on an unsaturated alpha-diketone monooxime or by reacting an alpha-ethylenic ketone, such as 2-butenone, and a nitrile oxide. The aforementioned methods are not particularly attractive inasmuch as the starting materials are different to prepare. Moreover, nitrile oxides are generally unstable materials and a main difficulty, apart from the threat of explosion, resides in the nitrile oxide's rapid spontaneous polymerization or dimerization to furoxans.

It is therefore an object of this invention to provide a novel method for the prepartioon of acylisoxazolines.

It is another object of this invention to provide a method for the preparation of acylisoxazolines from alkenes by a one step reaction.

Yet another object of this invention is to provide a method for the preparation of acylisoxazolines in good yields.

Other objects and advantages will become apparent from a reading of the following detailed description and examples.

SUMMARY OF THE INVENTION

Broadly, this invention contemplates a method of preparing an acylisoxaline which comprises contacting an alkene with dinitrogen tetroxide and oxygen in the presence of a denitrating agent and calcium oxide.

According to this invention, the acylisoxazolines are prepared from 1-alkenes of the formula $R-CH=CH_2$ where R is an alkyl group having from 2 to 20 carbon atoms. Illustrative of the alkenes we mention, 1-butene, 1-pentene, 1-hexene, 1-heptene, 1-octene, 1-decene, 1-dodecene, 1-tetradecene, 1-hexadecene and 1-eicosene. Mixture of alkenes such as propylene and 1-butene, or 1-pentene and 1-hexene or 1-tetradecene and 1-hexadecene or mixtures of $C_{10}$ to $C_{16}$ or $C_{14}$ to $C_{16}$ alkenes are also contemplated.

The 1-alkene employed in the method is contacted with dinitrogen textroxide and oxygen at a temperature between about $-10°$ and $40°$ C., preferably between about $5°$ and $25°$ C. The use of temperatures below about $-10°$ C. require costly and extensive refrigeration and at temperatures above $40°$ C. the threat of explosion exists. The mole ratio of the above components, namely the mole ratio of alkene to dinitrogen tetroxide to oxygen should be between about 1:0.02:0.04 and 1:0.4:30 to provide good yields of acylisoxazoline. It will be understood that dinitrogen tetroxide is an equilibrium mixture of dinitrogen tetroxide and nitrogen dioxide with the equilibrium driven essentially to 100percent dinitrogen tetroxide at $0°$ C. and essentially 100percent nitrogen dioxide at $140°$ C. The term dinitrogen tetroxide as used herein denotes the equilibrium mixtures as well as the pure $N_2O_4$ compound. The oxygen used in the present method may be air or essentially 100 percent oxygen or oxygen enriched air or oxygen in admixture with inert gases such as nitrogen or argon. However, an important aspect of the above reactant ratio are the moles of alkene to dinitrogen tetroxide employed. When 2 moles or less of alkene per mole of dinitrogen tetroxide are employed, that is, the mole ratio of alkene to $N_2O_4$ is about 1:0.5 to, for example, about 1:1.5, the yield of acylisoxazoline is severely reduced and the product additionally comprises substantial amounts of nitroketone, nitronitrate or nitroalcohol. Preferably, the mole ratio of alkene to $N_2O_4$ ranges from about 1:0.3 and 1:0.05. Oxygen in excess of that set out in the range above can be employed and does not detrimentally affect the reaction.

As described above, the alkene, dinitrogen tetroxide and oxygen are contacted in the presence of a denitrating agent and calcium oxide where the mole ratio of dinitrogen tetroxide to denitrating agent to calcium oxide is about 1:0.5:0.5 to about 1:5:5, preferably about 1:1:1 to about 1:2:2. Denitrating agents contemplated in the instant method include one or more members corresponding to the group consisting of:

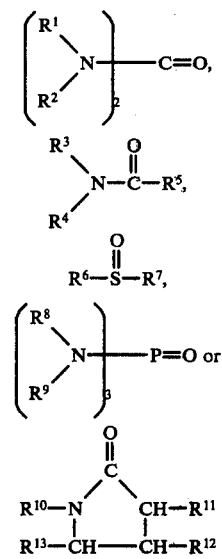

where $R^1$, $R^2$, $R^6$, $R^7$, $R^8$, $R^9$ and $R^{10}$ are alkyl of from 1 to 5 carbons and $R^3$, $R^4$, $R^5$, $R^{11}$, $R^{12}$ and $R^{13}$ are hydrogen or alkyl of from 1 to 5 carbons. Specific examples of denitrating agents include dimethylformamide, diethylformamide, dimethylacetamide, dimethylsulfoxide, diethylsulfoxide, tetramethylurea, tetraethylurea, hexamethylenephosphoramide, 1-methyl-2-pyrrolidinone and 1-ethyl-2-pyrrolidinone. Preferred denitrating agents are dimethylformamide, dimethylsulfoxide and 1-methyl-2-pyrrolidinone.

In the practice of the instant method, the reactants need not be added in any specific order. For example, to dinitrogen tetroxide, oxygen and alkene, there can be introduced the denitrating agent and calcium oxide optionally along with additional alkene. Alternatively, to the alkene and calcium oxide, one can introduce dinitrogen tetroxide, oxygen and denitrating agent. In our preferred manner of operation, to the alkene, denitrating agent and calcium oxide there is introduced dinitrogen tetroxide and oxygen. Under the conditions described above, the use of higher amounts of alkene functions as the reaction medium and enables the reactants to be suitably contacted desirably under conditions of agitation. The reaction can also be conducted in the presence of an inert liquid diluent as for example an aprotic organic solvent having a boiling point of between about $30°$ and $100°$ C. Such as n-hexane, n-heptane, carbon tetrachloride and diethylether. In general, reaction times can vary from about 1 to 5 hours employing reaction temperatures of from −10° to 40° C. leading to the production of the acylisoxazoline. At the completion of the reaction, inert diluent, if employed, can be removed from the reaction product by distillation. The acylisoxazoline, calcium oxide and any by-products can be separated, for example, by quenching in dilute hydrogen chloride solution followed by extraction with an organic solvent such as diethylether. The organic layer contains the desired product and the aqueous layer contains the denitrating agent, nitric acid and calcium salt.

The acylisoxazolines prepared according to this invention correspond to the formula:

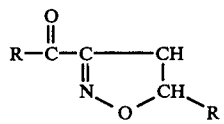

where R is as defined above. It will be understood that the 3-acyl-5-alkylisoxazolines prepared by the method described herein produces compounds where R in the acyl group can be the same or different than R in the alkyl group. For example, where the 1-alkene of choice is 1-hexadecene, R in the acyl and alkyl groups will be the same. When mixtures of 1-alkenes are utilized, for example 1-tetradecene and 1-hexadecene, R in the acyl and alkyl groups can be respectively of different carbon chain length. Illustrative of the acylisoxazolines provided by the instant method we mention 3-propanoyl-5-ethylisoxazoline, 3-butanoyl-5-propylisoxazoline, 3-butanoyl-5-octylisoxazoline, 3-pentanoyl-5-butylisoxazoline, 3-pentanoyl-5-tetradecylisoxazoline, 3-hexanoyl-5-pentylisoxazoline, 3-heptanoyl-5-tetradecylisoxazoline, 3-heptanoyl-5-hexylisoxazoline, 3-heptanoyl-5-dodecylisoxazoline, 3-nonanoyl-5-octylisoxazoline, 3-nonanoyl5-propylisoxazoline, 3-undecanoyl-5-decylisoxazoline, 3-undecanoyl-5-butylisoxazoline, 3-tridecanoyl-5-dodecylisoxazoline, 3-tridecanoyl-5-hexylisoxazoline, 3-pentadecanoyl-5-tetradecylisoxazoline, 3-pentadecanoyl-5-dodecylisoxazoline, 3-heptadecanoyl-5-hexadecylisoxazoline, 3-heptadecanoyl-5-decylisoxazoline, and 3-nonadecanoyl-5-octadecylisoxazoline.

The acylisoxazolines prepared by the method of this invention are useful as rust or oxidation inhibitors and as additives to fuels and lubricants. Corrosion inhibiting compositions wherein the acylisoxazolines can be utilized are described in, for example, U.S. Pat. No. 2,564,423. The compounds are also useful as intermediates in the preparation of other valuable products as amine derivatives and other derivatives are useful as photographic sensitizers and dyes for color photography.

In order to more fully illustrate the nature of our invention and the manner of practicing the same, the following examples are presented.

EXAMPLE 1

To a mixture of 45 grams of 1-hexadecene (0.20 mole), 3.0 grams of calcium oxide (0.054 mole), 5.0 grams of 1-methyl-2-pyrrolidinone (0.05 mole) and 20 milliliters of carbon tetrachloride as inert diluent, there was added simultaneously 0.5 mole of oxygen and 0.025 mole of dinitrogen tetroxide over a period of about 2 hours at about 5° to 10° C. At the completion of the dinitrogen tetroxide and oxygen additions, the solution was added to 100 milliliters of water and 100 milliliters of 50% HCl solution. The mixture was extracted with four 100 milliliter portions of diethylether and the ether layer was dried and stripped of solvent and unreacted alkene. The residue, 9.6 grams, corresponding to a yield of about 80 percent based on the dinitrogen tetroxide employed, was identified by infrared and nuclear magnetic resonance analysis to be 3-pentadecanoyl-5-tetradecylisoxazoline.

EXAMPLE 2

Following the procedure of Example 1, to a mixture of 8 grams of 1-hexadecene (0.036 mole), 3.0 grams of calcium oxide (0.05 mole) and 5.0 grams of 1-methyl-2-pyrrolidinone (0.05 mole) and 70 milliliters of carbon tetrachloride, there was introduced simultaneously 0.5 mole of oxygen and 0.025 mole of dinitrogen tetroxide over a period of 2 hours at about 10° C. The product (6.5 grams) was recovered as in Example 1 and was identified as a mixture of about 30 percent 3-pentadecanoyl-5-tetradecylisoxazoline, 20 percent 1-nitro-2-hexadecanone and the remainder essentially unconverted 1-hexadecene.

EXAMPLE 3

Following the procedure of Example 1, to a mixture of 4.0 grams of 1-hexadecene (0.018 mole), 2.0 grams of calcium oxide (0.036 mole) and 4.0 grams of 1-methyl-2-pyrrolidinone (0.036 mole) and 50 milliliters of carbon tetrachloride, there was introduced simultaneously 0.5 mole of oxygen and 0.05 mole of dinitrogen tetroxide over a period of 2 hours at about 15° C. The product (5.0 grams) was recovered as in Example 1 and was identified as a mixture of about 15 percent 3-pentadecanoyl-5-tetradecylisoxazoline, 10 percent 1-nitro-2-hexadecanone, 60 percent 1-nitro-2-hexadecylnitrate and 15 percent 1-nitro-2-hexadecanol.

EXAMPLE 4

To a mixture of 4.0 grams of 1-hexadecene (0.018 mole) in 50 milliliters of carbon tetrachloride there was added simultaneously 0.5 mole of oxygen and 0.020 mole of dinitrogen tetroxide over a period of about 2 hours at about 10° to 15° C. thereby forming 1-nitro-2-hexadecylperoxynitrate. The nitroperoxynitrate solution was thereafter added to a mixture 4.0 grams of 1-hexadecene (0.018 mole), 2.0 grams of calcium oxide (0.036 mole), 4.0 grams of 1-methyl-2-pyrrolidinone (0.036 mole) and 30 milliliters of carbon tetrachloride. The product (8.0 grams) was recovered as in Example 1 above and was identified as a mixture containing 3-pentadecanoyl-5-tetradecylisoxazoline (40 percent yield) and 1-nitro-2-hexadecanone (20 percent yield).

EXAMPLE 5

To a mixture of 4.0 grams of 1-hexadecene (0.018 mole), 2.0 grams of calcium oxide (0.036 mole), 4.0 grams of 1-methyl-2-pyrrolidinone (0.036 mole) and 50 milliliters of carbon tetrachloride, there was added over 2 hours 0.5 mole of oxygen and 0.02 mole of dinitrogen tetroxide at about 10° C. After recovering the product (4.1 grams) as in Example 1, the material was identified as 40 percent 1-nitro-hexadecanone, 30 percent 1-nitro-2-hexadecylnitrate and 30 percent 1-nitro-2-hexadecanol.

The example was repeated except that calcium oxide and 1-methyl-2-pyrrolidinone were replaced with 3.0 grams (0.04 mole) of dimethysulfoxide. The product was identified as 5 percent 3-pentadecanoyl-5-tetradecylisoxazoline, 70 percent 1-nitro-2-hexadecanone, 15 percent nitronitrate and 10 percent nitroalcohol.

The example was again repeated except that 30 grams (0.036 mole) of calcium oxide was employed and no denitrating agent at a reaction temperature of about 25° C. The product was identified as 50 percent nitroalcohol, 40 percent nitroketone and 10 percent nitronitrate.

The example was again repeated except that 1-methyl-2-pyrrolidinone was replaced with 3.0 grams (0.04 mole) of dimethylsulfoxide and the reaction conducted at about 15° C. The product was identified as 15 percent 3-pentadecanoyl-5-tetradecylisoxazoline, 45 percent nitroketone and 40 percent nitronitrate.

We claim:

1. A method of preparing an acylisoxazoline or mixtures thereof corresponding to the formula:

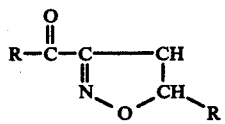

where R is an alkyl group having from 2 to 20 carbon atoms which comprises contacting a 1-alkene, or mixtures thereof, of the formula R—CH=CH$_2$ with dinitrogen tetroxide and oxygen in the presence of a denitrating agent that consists of one or more compounds selected from

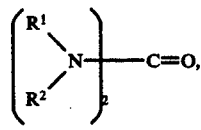

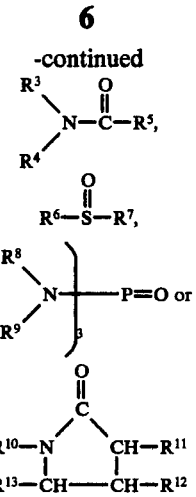

where $R^1$, $R^2$, $R^6$, $R^7$, $R^8$, $R^9$ and $R^{10}$ are alkyl of from 1 to 5 carbons and $R^3$, $R^4$, $R^5$, $R^{11}$, $R^{12}$, and $R^{13}$ are hydrogen or alkyl of from 1 to 5 carbons and calcium oxide at a temperature of about $-10°$ to 40° C., wherein the mole ratio of alkene to dinitrogen tetroxide to oxygen is from about 1:0.02:0.04 to 1:0.4:30 and the mole ratio of dinitrogen tetroxide to denitrating agent to calcium oxide is from about 1:0.5:0.5 to 1:5:5.

2. A method according to claim 1 wherein said contacting is at a temperature of about 5° to 25° C.

3. A method according to claim 1 wherein the mole ratio of alkene to dinitrogen tetroxide is about 1:0.05 to 1:0.3 and the mole ratio of dinitrogen tetroxide to denitrating agent to calcium oxide is from about 1:1:1 to 1:2:2.

4. A method according to claim 1 wherein said alkene is a mixture of alkenes.

5. A method according to claim 1 wherein said alkene is 1-hexadecene.

6. A method according to claim 1 wherein said alkene is 1-tetradecene.

7. A method according to claim 1 wherein said denitrating agent is 1-methyl-2-pyrrolidinone, dimethylsulfoxide, dimethylformamide, dimethylacetamide, or tetramethylurea.

8. A method according to claim 1 wherein said denitrating agent is 1-methyl-2-pyrrolidinone.

* * * * *